United States Patent [19]

Michel

[11] Patent Number: 4,548,924
[45] Date of Patent: Oct. 22, 1985

[54] ANTIBIOTICS M43B AND M43C, PHARMACEUTICAL COMPOSITION AND METHOD OF USE

[75] Inventor: Karl H. Michel, Indianapolis, Ind.

[73] Assignee: Eli Lilly and Company, Indianapolis, Ind.

[21] Appl. No.: 600,726

[22] Filed: Apr. 16, 1984

[51] Int. Cl.$^4$ .................... A61K 37/02; A61K 31/71; C07H 15/20
[52] U.S. Cl. .............................. 514/10; 260/112.5 R; 514/25; 536/16.8; 536/18.1
[58] Field of Search .............. 424/181; 536/16.8, 18.1; 260/112.5 R; 514/25, 10

[56] References Cited

U.S. PATENT DOCUMENTS 3,067,099 12/1962 McCormick et al. ................ 167/65

OTHER PUBLICATIONS

Donald J. McGraw, "The Antibiotic Discovery Era (1940–1960): Vancomycin as an Example of the Era", Thesis at Oregon State University, 1975, pp. 78–142.
F. J. Marshall, "Structure Studies on Vancomycin", J. Med. Chem. 8, 18–22, (1965).
G. M. Sheldrick et al., "Structure of Vancomycin and its Complex with Acetyl-D-alanyl-D-alanine", *Nature* 271, 223–225, (1978).
C. M. Harris, et al., "Structure of the Glucopeptide Antibiotic Vancomycin, Evidence for an Asparagine Residue in the Peptide", *J. Am. Chem. Soc.*, 104, pp. 4293–4295.
"Vancomycin and Factor A", Report by Eli Lilly and Company sent to the U.S. Food and Drug Administration on Mar. 5, 1963.
G. K. Best et al., "Chromatographic Separation of the Vancomycin Complex", *Antimicrob. Agents & Chemotherapy*-1968, 115–119.
R. R. Pfeiffer, "Structural Features of Vancomycin", in *Reviews of Infectious Diseases*, vol. 3, Supplement (1981).

Primary Examiner—Johnnie R. Brown
Attorney, Agent, or Firm—Nancy J. Harrison; Arthur R. Whale

[57] ABSTRACT

Antibiotics M43B and M43C, new glycopeptide antibiotics of the vancomycin class, are produced by *Nocardia orientalis* NRRL 2452. M43B and M43C have antibacterial activity.

12 Claims, No Drawings

ANTIBIOTICS M43B AND M43C, PHARMACEUTICAL COMPOSITION AND METHOD OF USE

SUMMARY OF THE INVENTION

Antibiotics M43B and M43C are new glycopeptide antibiotics produced by *Nocardia orientalis* NRRL 2452 and NRRL 2450. Antibiotics M43B and M43C and their salts have excellent activity against gram-positive microorganisms.

DETAILED DESCRIPTION

This invention relates to two new antibiotics called M43B and M43C, and to their salts. M43B has structural formula 1:

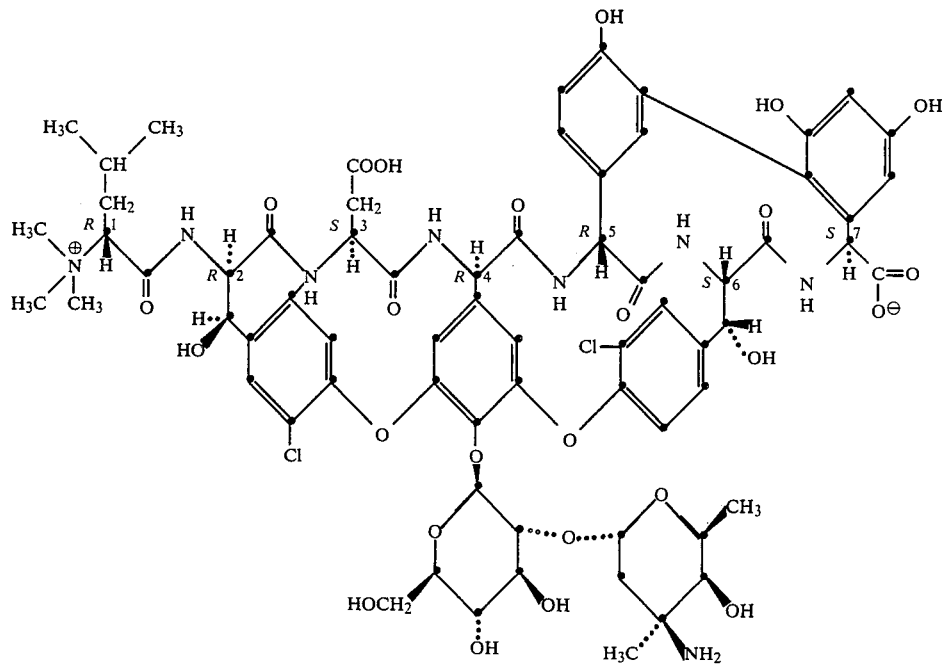

M43C has structural formula 2:

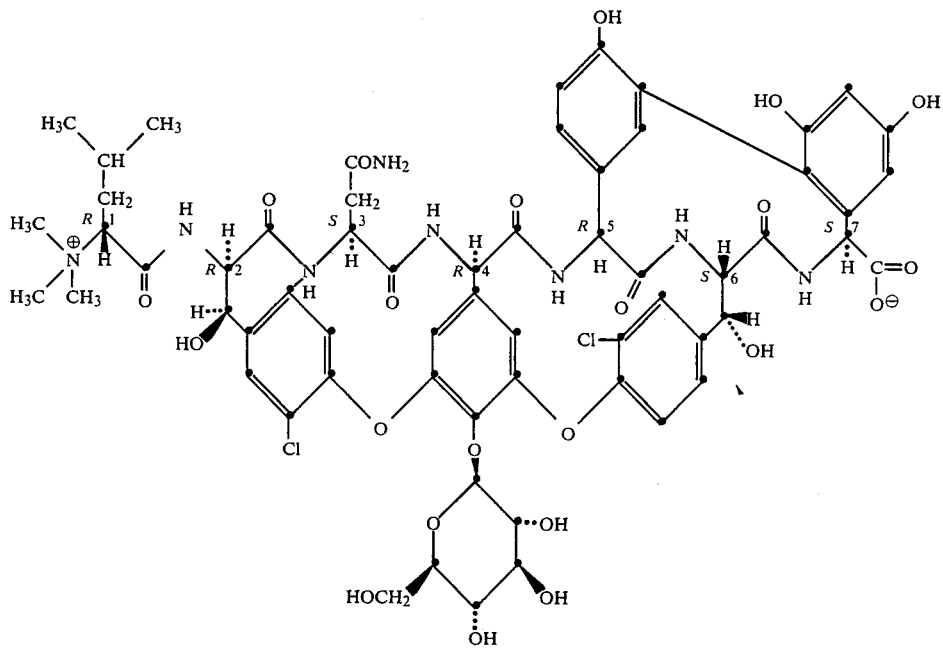

Antibiotics M43B and M43C and their salts have excellent antibacterial activity. The pharmaceutically acceptable salts of M43B and M43C are especially useful.

New, improved antibiotics are continually in demand, particularly for the treatment of human diseases. Increased potency, expanded spectrum of bacterial inhibition, increased in vivo efficacy, and improved pharmaceutical properties (such as greater oral absorption, higher blood or tissue concentrations, longer in vivo half life, and more advantageous rate or route of excretion and rate or pattern of metabolism) are some of the goals for improved antibiotics.

In the search for new antibiotics, structural modification of known antibiotics is attempted whenever possible. This approach is limited, however, to modifications which retain the desired activity. Many antibiotics, including the glycopeptides, have such complex structures that even small changes can be difficult to make by chemical means. The discovery of new antibiotics produced by fermentation processes continues, therefore, to be of great importance even in cases where the antibiotic, once recognized, is quite similar to a previously known antibiotic.

Antibiotics M43B and M43C are newly discovered members of the glycopeptide group of antibiotics. Closely related members of this group include vancomycin (see, for example, U.S. Pat. No. 3,067,099), ristocetin, antibiotic A51568 factors A and B (see the copending applications of M. M. Hoehn and G. G. Marconi, Ser. No. 562,255 filed Dec. 16, 1983 and LaVerne D. Boeck et al., Ser. No. 561,008, filed Dec. 13, 1983).

In U.S. Pat. No. 3,067,099, McCormick et al. described the preparation of vancomycin. Three strains of *Streptomyces orientalis*, two of which were numbered M43-05865 and M5-18260, were disclosed as being capable of making vancomycin. The cultures were deposited at what was then the Northern Regional Research Laboratories at Peoria, Ill., and were given the accession numbers NRRL 2450 (M43-05865) and 2452 (M5-18260). Later, the organism designation for the strains was changed from *Streptomyces orientalis* to *Nocardia orientalis*.

The vancomycin described in U.S. Pat. No. 3,067,099 became an important, commercially available antibiotic. The *N. orientalis* culture used to prepare commercial product was *N. orientalis* strain M5-18260 (NRRL 2452) or its progeny.

The structure of a closely related derivative of vancomycin was determined by Sheldrick et al [G. M. Sheldrick, P. G. Jones, O. Kennard, D. H. Williams and G. A. Smith, *Nature* 271 (5642), 223–225 (1978)]; later, the structure of vancomycin itself was found by Harris et al. [C. M. Harris and T. M. Harris, *J. Am. Chem. Soc.* 104, 4293–4295 (1982)] to be that shown in formula 3:

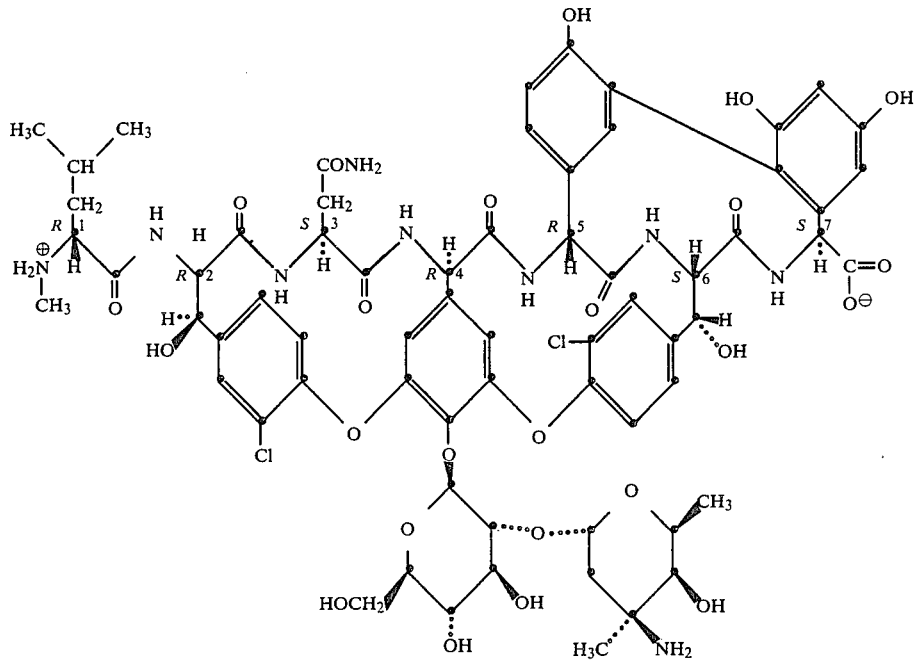

This invention relates to the discovery of antibiotic M43B and M43C, which are minor factors produced by the *N. orientalis* M5-18260 (NRRL 2452) strain. The antibiotic complex produced by *N. orientalis* M43-05865 (NRRL 2450), which is called the M43 antibiotic complex, appears to contain trace amounts of antibiotics M43B and M43C. Methods of making antibiotics M43B and M43C by fermentation of *N. orientalis* NRRL 2450 are described in the copending application of M. M. Hoehn and R. Nagarajan entitled METHODS FOR PRODUCING M43 ANTIBIOTICS, Ser. No. 600,728, filed herewith this even date.

In addition to vancomycin, the M43 complex contains another major factor which is the subject of a copending application of Harvey M. Higgins, Mack H. McCormick and Kurt E. Merkel entitled ANTIBIOTIC M43A, Ser. No. 600,729, filed herewith this even date, and a number of minor factors. Among the other minor M43 factors are (1) A51568 factor A of Hoehn et al., supra, and possibly A51568 factor B of Boeck et al., supra; (2) antibiotic M43D, which is the subject of a copending application of Kurt E. Merkel entitled ANTIBIOTIC M43D, Ser. No. 600,725, filed herewith this even date; and (3) the compounds designated agluco-A51568A, aglucovancomycin and agluco-M43A, and possibly desvancosaminevancomycin, all of which are disclosed in the copending application of R. Nagarajan and A. Schabel entitled NOVEL GLYCOPEPTIDE ANTIBIOTICS, Ser. No. 600,727, also filed herewith this even date. The structural relationships of the M43 antibiotics are provided in formulas 1–12 which follow:

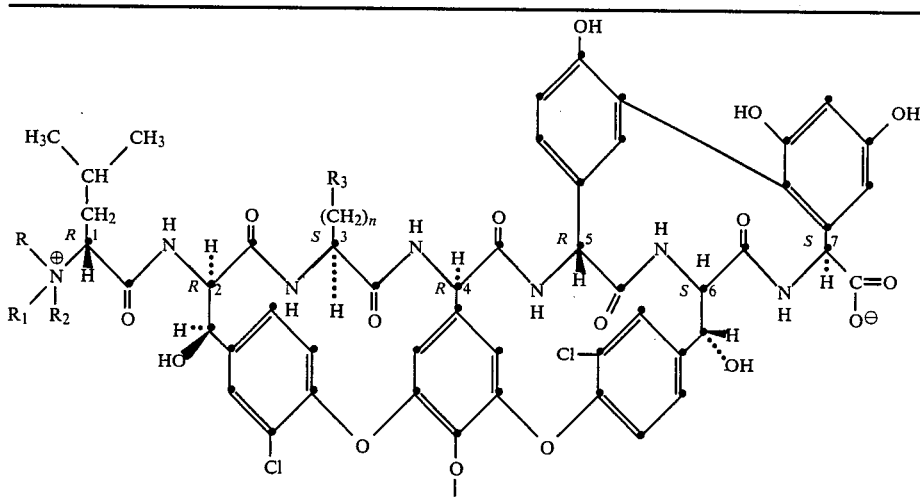

| Compound No. | Compound | R | $R_1$ | $R_2$ | $R_3$ | n | $R_4$ |
|---|---|---|---|---|---|---|---|
| 1 | M43B | $CH_3$ | $CH_3$ | $CH_3$ | COOH | 1 | vancosaminyl-O—glucosyl |
| 2 | M43C | $CH_3$ | $CH_3$ | $CH_3$ | $CONH_2$ | 1 | glucosyl |
| 3 | Vancomycin | H | H | $CH_3$ | $CONH_2$ | 1 | vancosaminyl-O—glucosyl |
| 4 | M43A | $CH_3$ | $CH_3$ | $CH_3$ | $CONH_2$ | 1 | vancosaminyl-O—glucosyl |
| 5 | M43D | H | $CH_3$ | $CH_3$ | $CONH_2$ | 1 | vancosaminyl-O—glucosyl |
| 6 | Agluco-A51568A | H | H | H | $CONH_2$ | 1 | H |
| 7 | Aglucovancomycin | H | H | $CH_3$ | $CONH_2$ | 1 | H |
| 8 | Agluco-M43A | $CH_3$ | $CH_3$ | $CH_3$ | $CONH_2$ | 1 | H |
| 9 | Desvancosamine-A51568A | H | H | H | $CONH_2$ | 1 | glucosyl |
| 10 | Desvancosamine-Vancomycin | H | H | $CH_3$ | $CONH_2$ | 1 | glucosyl |
| 11 | A51568A | H | H | H | $CONH_2$ | 1 | vancosaminyl-O—glucosyl |
| 12 | A51568B | H | H | H | $CONH_2$ | 2 | vancosaminyl-O—glucosyl |

M43B and M43C, the new glycopeptide antibiotics of this invention, are close to vancomycin in structure and also in activity. They are, therefore, valuable additions to this group of antibiotics.

M43B and M43C are shown in formulas 1 and 2 as zwitterions. Those in the art will recognize, however, that each has one or two carboxyl groups, one or two amino groups and three phenolic groups which can react to form various salts. All such forms of M43B and M43C are part of this invention. The salts are useful, for example, for separating and purifying the antibiotics. In addition, the salts have an improved solubility in water.

M43B and M43C salts are prepared using standard procedures for salt preparation. For example, the M43B zwitterion can be neutralized with an appropriate acid to form an M43B acid addition salt.

The acid addition salts of M43B and M43C are particularly useful. Representative suitable salts include those salts formed by standard reactions with both organic and inorganic acids such as, for example, sulfuric, hydrochloric, phosphoric, acetic, succinic, citric, lactic, maleic, fumaric, cholic, pamoic, mucic, D-glutamic, d-camphoric, glutaric, glycolic, phthalic, tartaric, formic, lauric, stearic, salicylic, methanesulfonic, benzenesulfonic, sorbic, picric, benzoic, cinnamic and like acids.

Pharmaceutically acceptable acid addition salts are an especially preferred group of salts of this invention.

Antibiotics M43B and M43C are prepared by culturing *Nocardia orientalis* NRRL 2450 or NRRL 2452, or an M43B or M43C-producing variant, mutant or recombinant thereof, under submerged aerobic conditions in a suitable culture medium until a substantial amount of M43B or M43C is produced. The culture medium used to grow *Nocardia orientalis* NRRL 2450 or NRRL 2452 can be one of a number of media. For economy in production, optimal yield, and ease of product isolation, however, certain culture media are preferred. Thus, for example, preferred carbon sources include carbohydrates such as dextrin, dextrose, glucose and glycerol. Preferred nitrogen sources include enzyme digests of casein, cottonseed meal, soybean grits, protein peptones and the like. Among the nutrient inorganic salts which can be incorporated in the culture media are the customary soluble salts capable of yielding iron, potassium, sodium, magnesium, calcium, ammonium, chloride, carbonate, sulfate, nitrate, and like ions.

Essential trace elements necessary for the growth and development of the organism should also be included in the culture medium. Such trace elements commonly occur as impurities in other constituents of the medium in amounts sufficient to meet the growth requirements of the organism. It may be necessary to add small amounts (i.e. 0.2 ml/L) of an antifoam agent such as polypropylene glycol (M.W. about 2000) to large-scale fermentation media if foaming becomes a problem.

For production of substantial quantities of antibiotics M43B and M43C, submerged aerobic fermentation in tanks is preferred. Small quantities may be obtained by shake-flask culture. Because of the time lag in antibiotic production commonly associated with inoculation of large tanks with the spore form of the organism, it is preferable to use a vegetative inoculum. The vegetative inoculum is prepared by inoculating a small volume of culture medium with the spore form or mycelial fragments of the organism to obtain a fresh, actively growing culture of the organism. The vegetative inoculum is then transferred to a larger tank. The medium used for the vegetative inoculum can be the same as that used for larger fermentations, but other media can also be used.

*N. orientalis* NRRL 2450 and NRRL 2452 can be grown at temperatures between about 25° and about 37° C. Optimum antibiotic production appears to occur at temperatures of about 30° C.

As is customary in aerobic submerged culture processes, sterile air is bubbled through the culture medium. For efficient antibiotic production the percent of air saturation for tank production should be about 50% or above (at 30° C. and about 5 psi of back pressure).

Antibiotic production can be followed during the fermentation by testing samples of the broth against organisms known to be sensitive to the antibiotics. One useful assay organism is *Staphylococcus aureus* NRRL B313. In addition, antibiotic production can be monitored by HPLC with UV detection.

Following their production under submerged aerobic fermentation conditions, antibiotics M43B and M43C can be recovered from the fermentation medium by filtering the broth to remove mycelia and purifying the filtered broth by a series of adsorptions on suitable adsorbents, such as an ion-exchange resins, chemically modified hydrophobic inorganic supports used in high performance reversed-phase liquid chromatography, and high porosity polymers, eluting the M43B and M43C in each case with a suitable solvent such as aqueous acetonitrile.

A preferred method of preparing M43C is described by Nagarajan and Schabel in their copending application, supra. This method comprises treating M43A with trifluoroacetic acid (TFA) at a temperature of about −15° C. for about 16 hours.

M43B and M43C inhibit the growth of a broad spectrum of pathogenic bacteria, especially gram-positive bacteria. Table I summarizes the minimal inhibitory concentrations (MIC's) at which M43B and M43C inhibit certain organisms, as determined by standard agar-dilution assays.

TABLE I

In Vitro Activity of M43B and M43C

| Organism | MIC (mcg/ml) M43B | MIC (mcg/ml) M43C |
|---|---|---|
| *Staphylococcus aureus* NRRL B313 | 16 | 2 |
| *Staphylococcus aureus* V41 | 32 | 4 |
| *Staphylococcus aureus* X400 | 32 | 4 |
| *Staphylococcus aureus* S13E | 32 | 4 |
| *Staphylococcus epidermidis* EPI1 | 32 | 8 |
| *Staphylococcus epidermidis* 222 | 32 | 8 |
| *Streptococcus pyogenes* C203 | 16 | 2 |
| *Streptococcus pneumoniae* Park 1 | 2 | 2 |
| *Streptococcus faecium* ATCC 9790 | 32 | 4 |
| *Streptococcus* sp. group D 2041 | 32 | 8 |
| *Haemophilus influenzae* C.L. | >64 | >64 |
| *Haemophilus influenzae* 76 | >64 | 32 |
| *Escherichia coli* N10 | >64 | >64 |
| *Escherichia coli* EC14 | >64 | >64 |
| *Escherichia coli* TEM | >64 | >64 |
| *Klebsiella pneumoniae* X26 | >64 | >64 |
| *Klebsiella pneumoniae* X68 | >64 | >64 |
| *Klebsiella pneumoniae* KAE | >64 | >64 |

M43C has also shown in vivo antimicrobial activity against an experimental bacterial infection. When two doses of test compound were administered to mice in experimental infections, the activity observed was measured as an $ED_{50}$ value [effective dose in mg/kg to protect 50% of the test animals: see Warren Wick, et al., *J. Bacteriol.* 81, 233-235 (1961)]. The $ED_{50}$ value observed for M43C is given in Table II.

TABLE II $ED_{50}$ Value for M43C

| Organism | Route of Administration | $ED_{50}$ (mg/kg/2)[a] M43C |
|---|---|---|
| *Streptococcus pneumoniae* | subcutaneous | 2.67 |

[a]LD Challenge Dose = 125

Pharmaceutical formulations of M43B, M43C, or salts of M43B or M43C (an M43 compound) are also part of this invention. The antibiotic, preferably as a pharmaceutically acceptable salt, can be formulated for oral or parenteral administration for the therapeutic or prophylactic treatment of bacterial infections. For example, an M43 compound can be admixed with conventional pharmaceutical carriers and excipients and used in the form of tablets, capsules, elixirs, suspensions, syrups, wafers and the like. The compositions comprising an M43 compound will contain from about 0.1 to about 90% by weight of the active compound, and more generally from about 10 to about 30%. The compositions may contain common carriers and excipients, such as corn starch or gelatin, lactose, sucrose, microcrystalline cellulose, kaolin, mannitol, dicalcium phosphate, sodium chloride and alginic acid. Disintegrators commonly used in the formulations of this invention include croscarmellose sodium, microcrystalline cellulose, corn starch, sodium starch glycolate and alginic acid. Tablet binders that can be included are acacia, methylcellulose, sodium carboxymethylcellulose, polyvinylpyrrolidone (Povidone), hydroxypropyl methylcellulose, sucrose, starch and ethylcellulose. Lubricants that can be used include magnesium stearate or other metallic stearates, stearic acid, silicone fluid, talc, waxes, oils and colloidal silica. Flavoring agents such as peppermint, oil of wintergreen, cherry flavoring or the like can also be used. It may be desirable to add a coloring agent to make the dosage form more esthetic in appearance or to help identify the product.

For intravenous (IV) use, a water soluble form of the antibiotic can be dissolved in one of the commonly used intravenous fluids and administered by infusion. Such fluids as, for example, physiological saline, Ringer's solution or 5% dextrose solution can be used.

For intramuscular preparations, a sterile formulation of a suitable soluble salt form of the antibiotic, for example the hydrochloride salt, can be dissolved and administered in a pharmaceutical diluent such as Water-for-Injection, physiological saline or 5% glucose solution. A suitable insoluble form of the antibiotic may be prepared and administered as a suspension in an aqueous base or a pharmaceutically acceptable oil base, e.g. an ester of a long chain fatty acid such as ethyl oleate.

For oral use, a sterile formulation of a suitable salt form of the antibiotic, for example, the hydrochloride salt, formulated in a diluent such as distilled or deionized water, is particularly useful.

Alternatively, the unit dosage form of the antibiotic can be a solution of the antibiotic or preferably a salt thereof in a suitable diluent in sterile, hermetically sealed ampoules. The concentration of the antibiotic in the unit dosage may vary, e.g. from about 1 percent to about 50 percent depending on the particular form of the antibiotic and its solubility and the dose desired by the physician.

In a further aspect, this invention provides a method for treating or controlling infectious diseases, especially those caused by gram-positive microorganisms, in animals. This method comprises administering to the animal an effective dose of an M43 compound. An effective dose is generally between about 1 and about 200 mg/kg of a pharmaceutically acceptable M43 compound. A preferred dose is from about 20 to about 120 mg/kg of M43 compound. A typical daily dose for an adult human is from about 500 mg to about 2.0 g.

In practicing this method, the antibiotic can be administered in a single daily dose or in multiple doses per day. The treatment regime may require administration over extended periods of time, e.g., for several days or for from two to three weeks. The amount per administered dose or the total amount administered will depend on such factors as the nature and severity of the infection, the age and general health of the patient, the tolerance of the patient to the antibiotic and the microorganism or microorganisms involved in the infection.

A convenient method of practicing the treatment method is to administer the antibiotic via IV infusion. In this procedure a sterile formulation of a suitable soluble salt of the antibiotic is incorporated in a solution of a physiological fluid, such as 5% dextrose solution, and the resulting solution is infused slowly IV. Alternatively, the piggy-back method of IV infusion can be used.

In another embodiment, this invention relates to methods of increasing feed-utilization efficiency in poultry, swine, sheep and cattle, of promoting growth rates in cattle raised for meat production and of enhancing milk production in lactating ruminants. For increasing feed utilization efficiency and promoting growth, an M43 compound is administered orally in a suitable feed in an amount of from about 2 to about 200 grams per ton of total feed. For beef cattle, for example, a range of about 12 to 3000 mg/head/day is suitable. For enhancing milk production in lactating ruminants, oral administration of a daily amount of from about 0.04 to about 16 mg/kg of body weight (or about 25 to about 5000 mg/ruminant/day) is suggested.

The following examples are provided to illustrate this invention:

EXAMPLE 1

Isolation of Antibiotics M43A, M43B and M43C from *N. orientalis* NRRL 2452

A. Separation from Vancomycin

Using the procedure in U.S. Pat. No. 3,067,099 (Example 2), fourteen 1200 gallon fermenters were processed to give a crude preparation in the hydrochloride salt form. This prepearation was further separated on a Dowex 50-2X resin column, selectively eluting fractions containing M43A with a 2-percent aqueous ammonium formate solution (pH 9.6) as the eluent, to give a semi-purified preparation containing M43A, M43B and M43C.

B. Separation of M43A, M43B and M43C

A portion (15 g) of material prepared as in Section A was dissolved in water (1.5 L), filtered, and applied to a CM-Sephadex C-25 ($NH_4^+$) column (glass, 6-×77-cm, packed with 2 L of resin in water). The column was washed with water (2.5 L) at a rate of 5–10 ml/min to remove impurities. The column was then developed using a linear gradient of (a) 8 liters of water in the mixing chambers and (b) 8 liters of 2M $NH_4HCO_3$ in the reservoir. Elution was monitored by assay against *Bacillus subtilis* in minimal media. Key fractions were also analyzed by analytical HPLC. The M43B- and M43C-containing fractions were combined, desalted on HP-20, concentrated and lyophilized to give 50 mg of enriched material. This material was applied to a reversed phase silica gel column (LP1-C-18) which was eluted with a $CH_3CN$ (13%):aqueous 0.05M $KH_2PO_4$, pH 3.2 (87%) solvent system, eluting at a flow rate of 2.5-ml/min. Fractions were monitored by analytical HPLC. The M43B-containing fractions were combined, desalted and lyophilized to give 14.6 mg of antibiotic M43B. The M43C-containing fractions were combined, desalted and lyophilized to give 6.2 mg of M43C.

C. Characteristics of M43B

M43B has an integer molecular weight of 1476 as determined by fast-atom-bombardment mass spectrometry.

The molecular structure of M43B, as shown in formula 1, is based on proton nuclear magnetic resonance (NMR) studies.

D. Characteristics of M43C

M43C has an integer molecular weight of 1332 as determined by fast-atom-bombardment mass spectrometry. The molecular weight of M43C is 143 units lower than that of M43A (m.w. 1475). This is consistent with the structural difference between M43A and M43C being the presence of an additional vancosomine in M43A.

The molecular structure of M43C, as shown in formula 2, was deduced in part from $^1H$ NMR studies.

The proton NMR assignments for M43C are summarized in Table III. The chemical shifts listed in Table III were obtained in DMSO-$d_6$ solution at 60° C. and at 360 MHz proton frequency. The numbering scheme used is shown in formula 13:

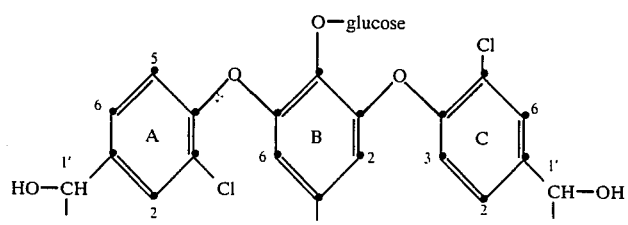

-continued

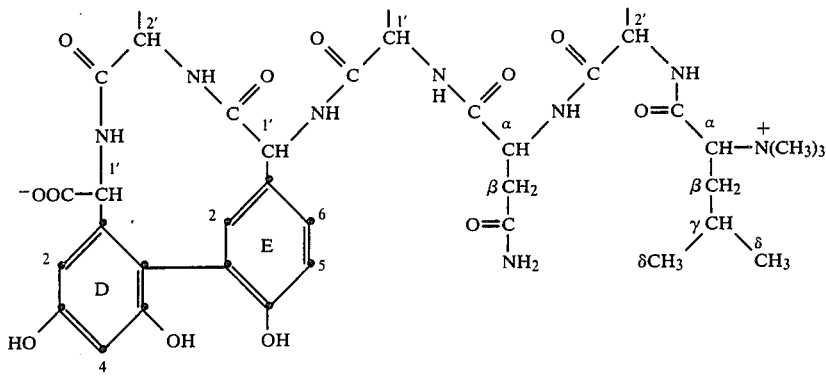

TABLE III

| Proton NMR Assignments for M43C[a] | |
|---|---|
| Assignment | Chem. Shift |
| A-NH | 6.45 |
| A-2' | 4.15 |
| A-1' | 5.21 |
| A-2 | 7.86 |
| A-5 | 7.24 |
| A-6 | 7.46 |
| B-NH | 8.81 |
| B-1' | 5.76 |
| B-2 | 5.67 |
| B-6 | 5.21 |
| C-NH | 10.32 |
| C-2' | 4.92 |
| C-1' | 5.14 |
| C-2 | 7.52 |
| C-3 | 7.18 |
| C-6 | 7.43 |
| D-NH | 8.29 |
| D-1' | 4.41 |
| D-2 | 6.34 |
| D-4 | 6.45 |
| E-NH | 8.40 |
| E-1' | 4.45 |
| E-2 | 7.16 |
| E-5 | 6.68 |
| E-6 | 6.75 |
| Asn-NH | ~6.45 |
| Asn-α | 4.37 |
| Asn-β's | 2.48 and |
| " | 2.12 |
| $\underset{\text{Asn-C-NH}_2}{\overset{O}{\|}}$ | 7.29 and |
| " | 6.72 |
| Leu-$\overset{+}{\text{N}}$(CH$_3$)$_3$ | 3.20 |
| Leu-α | 4.72 |
| Leu-β's | 1.91 and |
| | 1.59 |
| Leu-γ | 1.46 |
| Leu-δ's | 0.93 and |
| | 0.87 |
| Glucose #1 | 5.32 |
| #2 | 3.40 |
| #5 | 3.24 |
| #6 | 3.53 and |
| | 3.70 |

[a]Phenols not yet assigned

EXAMPLE 2

Shake-flask Fermentation of *N. orientalis* M43-05865 to Produce M43B and M43C

A lyophilized pellet of *Nocardia orientalis* M43-05865 (NRRL 2450) is dispersed in 1-2 ml of sterilized water. This solution (<0.1 ml) is used to inoculate an agar slant having the following composition:

| Ingredient | Amount (g/L.) |
|---|---|
| Dextrin | 10 |
| Enzymatic hydrolysate of casein[a] | 2 |
| Beef extract | 1 |
| Yeast extract | 1 |
| Agar | 20 |
| Distilled water q.s. to | 1 liter |

[a]N-Z Amine A, Humko Sheffield Chemical, Lyndhurst NJ

The inoculated slant is incubated at 30° C. for 4–6 days. The mature slant culture is covered with sterile distilled water and scraped with a loop to loosen the spores. The resulting spore suspension (1 ml) is used to inoculate 100 ml of a vegetative medium having the following composition:

| Ingredient | Amount (g/L.) |
|---|---|
| Glucose | 15 |
| Soybean meal | 15 |
| Cornsteep solids | 5 |
| CaCO$_3$ | 2 |
| NaCl | 5 |
| Tap H$_2$O q.s. to | 1 liter |

The inoculated vegetative medium is incubated in a 500-ml Erlenmeyer flask for 24–48 hours at 30° C. on a reciprocal shaker with a 2-inch stroke at 108 RPM or on a rotary shaker operating at 250 RPM.

This incubated vegetative medium (5 ml) is used to inoculate 100 ml of a sterilized (120° C. for 30 minutes) production medium having the following composition:

| Ingredient | Amount (g/L.) |
|---|---|
| Glucose | 10 |
| Edible molasses | 20 |
| Peptone[a] | 5 |
| CaCO$_3$ | 2 |
| Tap H$_2$O q.s. to | 1 liter |

[a]Bacto (Difco Laboratories, Detroit, MI)

The inoculated fermentation medium is incubated in a 500-ml Erlenmeyer flask at 25°–30° C. for 72–96 hours on either a rotary shaker operating at 250 RPM or a reciprocal shaker operating at 108 strokes per minute. The pH of the uninoculated medium varies with the medium used for production, but the production media of Examples 2–5 have an initial pH range of 6.0 to 7.5 and a harvest pH range of 6.5 to 8.0.

B. Isolation of M43 Complex

Whole broth (2 L.), prepared as described in Section A, was filtered. The filtrate was treated with a cation exchange resin (Dowex 50W-X4, H+, NH4+, pH 5.0), using 100-ml of resin and stirring batchwise for 30 minutes. The effluent was decanted and discarded. The resin was washed thoroughly with water, and the water wash was discarded. The resin was then eluted batchwise with 1N NH4OH (250 ml and 175 ml per batch). The eluates were combined and concentrated under vacuum to a volume of about 50 ml. An aliquot (2 ml) was removed for assay, and the remaining concentrate was lyophilized to give 300 mg of M43 complex.

C. Separation of M43B and M43C by Analytical HPLC

A portion of the M43 complex prepared as described in Section B is examined by analytical HPLC, using the following system:

Column: Beckman Ultrasphere (5μ particle size), ODS, 25 cm.
Mobile Phase: Solvent A: $CH_3CN/TEAP$ (5:95), Solvent B: $CH_3CN/TEAP$ (2:3).
[TEAP=0.5% aqueous triethylamine adjusted to pH 3 with conc. phosphoric acid].
Gradient: 9% B to 70% B over a 40-min period, then hold for 5 min. at 70% B.
Flow Rate: 1.0 ml/min.
Detection: UV at 254 nm.

| M43A Factor | Retention Time (min.) |
|---|---|
| A51568 factor B[a] | 5.92 |
| A51568 factor A | 8.96 |
| vancomycin | 12.23 |
| desvancosamine-A51568A | 17.59 |
| M43D | 19.96 |
| desvancosamine-vancomycin[a] | 20.38 |
| M43A | 24.26 |
| M43B[a] | 25.46 |
| M43C[a] | 29.58 |
| agluco A51568A | 36.97 |
| agluco-vancomycin | 37.72 |
| agluco-M43A | 39.79 |

[a]Trace amounts

EXAMPLE 3

Antibiotics M43B and M43C prepared according to the method of Example 2, but using the following production medium:

| Ingredient | Amount (g.L.) |
|---|---|
| Glucose | 10 |
| Yeast | 5 |
| Distillers solubles | 5 |
| KCl | 4 |
| $CaCO_3$ | 1 |
| Tap $H_2O$ q.s. to | 1 liter |

EXAMPLE 4

M43B and M43C prepared by the method of Example 2, but using the following production medium:

| Ingredient | Amount |
|---|---|
| Casamino acids | 5 g/L |
| Dextrin | 5 g/L |
| Glycerol | 5 g/L |
| Blackstrap molasses | 10 g/L |
| Yeast | 5 g/L |
| $K_2HPO_4$ | 1 g/L |
| Mineral Stock | 5 ml |
| Tap $H_2O$ q.s. to | 1 liter |

EXAMPLE 5

M43B and M43C prepared by the method of Example 2, but using the following production medium:

| Ingredient | Amount (g/L.) |
|---|---|
| Soybean meal | 15 |
| Casein | 1 |
| $NaNO_3$ | 3 |
| Glucose syrup | 20 |
| Tap $H_2O$ q.s. to | 1 liter |

EXAMPLE 6

Preparation of M43C

M43A (398 mg) was dissolved in TFA (10 ml). The resulting solution was kept at $-15°$ C. for 30 hours, and then was evaporated to dryness and freeze-dried. The reaction product was purified by reversed-phase HPLC using the system described in Example 2, Section C, to give 40 mg of M43C as identified by NMR and FABMS.

EXAMPLE 7

M43C Tablet Formulation

Preparation of tablets containing 250 mg of M43C:

| Ingredient | Weight |
|---|---|
| M43C diphosphate | 282.9 mg |
| Microcrystalline cellulose | 101.1 mg |
| Croscarmellose sodium | 12.0 mg |
| Providone | 12.0 mg |
| Magnesium stearate | 3.0 mg |
| Stearic acid | 4.0 mg |
| Purified water | 0.16 ml |

Add M43C diphosphate, a portion of the microcrystalline cellulose and a portion of the croscarmellose sodium to a suitable container and blend until homogenous. Prepare a solution of Povidone in water, and add the Povidone solution to the blended powders. Granulate the resulting mixture, size if necessary and dry. Add the remaining microcrystalline cellulose and croscarmellose sodium to the dried mixture and blend. Add magnesium stearate and stearic acid, and blend the mixture. Compress the resulting powder blend into tablets with a theoretical weight of 415 mg. Each tablet contains M43C diphosphate equivalent to 250 mg of M43C.

EXAMPLE 8

M43C Capsule Formulation

| Ingredient | Weight |
|---|---|
| M43C dihydrochloride | 262.2 mg |
| Corn starch flowable powder | 137.65 mg |
| Silicone fluid 350 centistokes | 2.75 mg |

| Ingredient | Weight |
| --- | --- |
| Corn starch | 147.1 mg |

Blend M43C dihydrochloride, starch flowable powder, silicone fluid 350 centistokes and starch powder in a suitable mixer until homogeneous. Fill into appropriate size hard gelatin capsules to a net fill weight of 550 mg. Each capsule contains M43C dihydrochloride equivalent to 250 mg of M43C.

EXAMPLE 9

M43C Suspension Formulation

Prepare M43C in a sterile insoluble form by crystallization or precipitation. Mill or screen to correct particle size for suspension. Suspend the antibiotic in the following vehicle:

| Ingredient | Amount |
| --- | --- |
| Lecithin | 1% |
| Sodium citrate | 2% |
| Propylparaben | 0.015% |
| Water for Injection | q.s. to desired volume. |

Sterilize the suspension. The suspension may be manufactured in the bulk and filled into vials or may be prepared by adding the vehicle to the M43C in the vial.

We claim:

1. Antibiotic M43B which has the formula

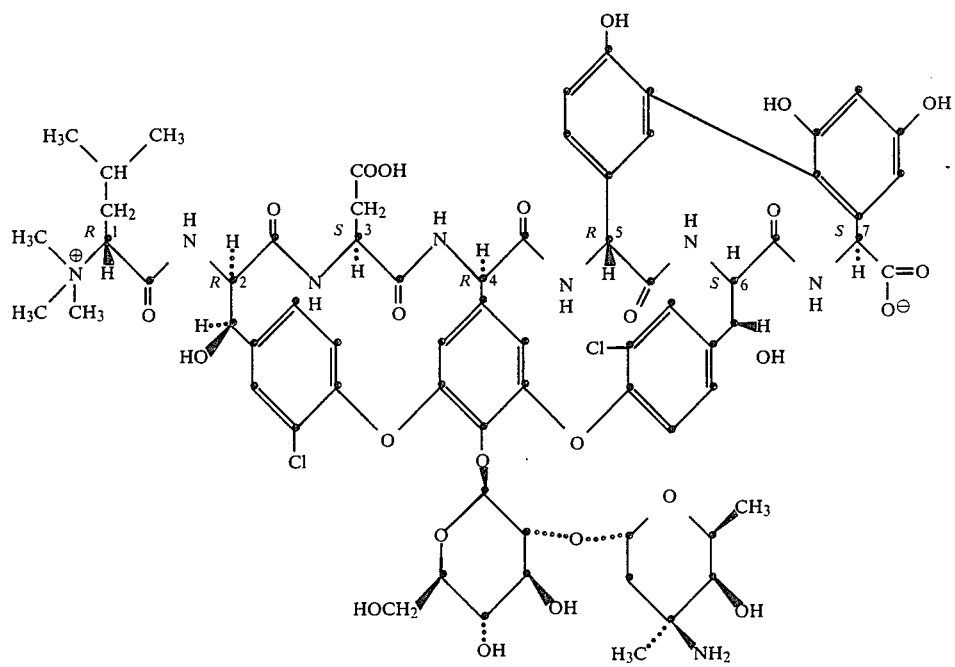

and its salts.

2. A salt of claim 1 which is pharmaceutically acceptable.

3. A compound of claim 1 wherein the salt is a phosphate salt.

4. A compound of claim 1 wherein the salt is a hydrochloride salt.

5. Antibiotic M43C which has the formula

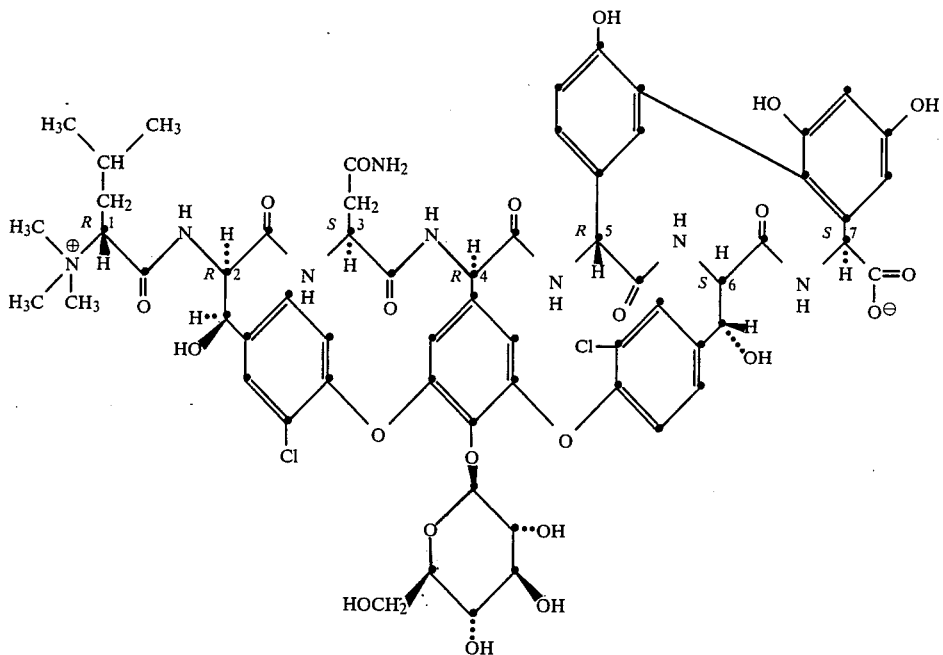

and its salts.

6. A salt of claim 1 which is pharmaceutically acceptable.

7. A compound of claim 1 wherein the salt is a phosphate salt.

8. A compound of claim 1 wherein the salt is a hydrochloride salt.

9. A composition useful for treating gram-positive bacterial infections comprising an effective antibacterial amount of antibiotic M43C or a pharmaceutically acceptable salt of M43C together with a suitable vehicle.

10. A method for treating infections caused by gram-positive bacteria which comprises administering an effective amount of a composition of claim 9 to an animal.

11. Antibiotic M43B of claim 1 in substantially pure form, and its salts.

12. Antibiotic M43C of claim 5 in substantially pure form, and its salts.

* * * * *

UNITED STATES PATENT AND TRADEMARK OFFICE
CERTIFICATE OF CORRECTION

PATENT NO. : 4,548,924

DATED : October 22, 1985

INVENTOR(S) : Karl H. Michel

It is certified that error appears in the above—identified patent and that said Letters Patent is hereby corrected as shown below:

Column 16, that portion of the structural formula appearing as

" 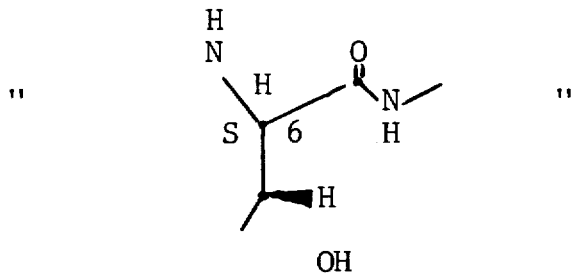 "

should read

-- 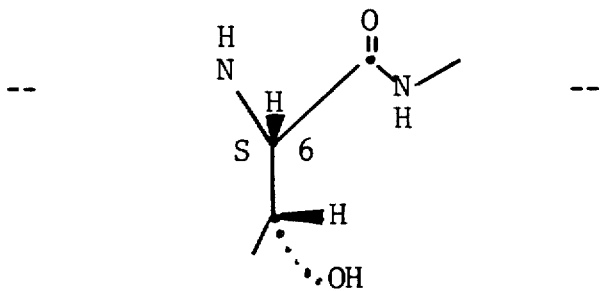 --

UNITED STATES PATENT AND TRADEMARK OFFICE
CERTIFICATE OF CORRECTION

PATENT NO. : 4,548,924

DATED : October 22, 1985

INVENTOR(S) : Karl H. Michel

It is certified that error appears in the above-identified patent and that said Letters Patent is hereby corrected as shown below:

Column 17, line 31, "claim 1" should read -- claim 5 --; line 33, "claim 1" should read -- claim 5 --; line 35, "claim 1" should read -- claim 5 --. Column 18, that portion of the structural formula appearing as

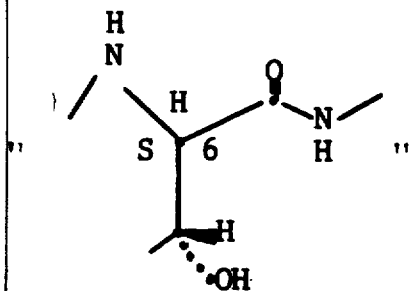  "  should read  --  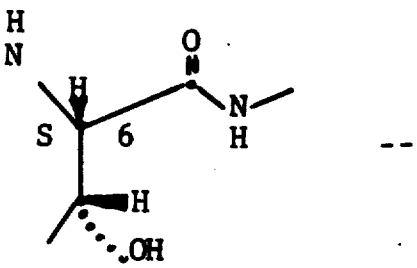  --

Signed and Sealed this

Eighteenth Day of March 1986

[SEAL]

Attest:

DONALD J. QUIGG

Attesting Officer

Commissioner of Patents and Trademarks